United States Patent
Suñé Negre et al.

(10) Patent No.: US 9,161,564 B2
(45) Date of Patent: Oct. 20, 2015

(54) NUTRITIONAL SUPPLEMENT COMPOSITION

(75) Inventors: Josep Maria Suñé Negre, Barcelona (ES); Raimon Cortada Pasola, Barcelona (ES); Manuel Roig Carreras, Barcelona (ES); Rocio Sarrate Arjona, Barcelona (ES)

(73) Assignee: VITAE NATURAL NUTRITION, S.L., Barcelona (ES)

( * ) Notice: Subject to any disclaimer, the term of this patent is extended or adjusted under 35 U.S.C. 154(b) by 0 days.

(21) Appl. No.: 13/211,537

(22) Filed: Aug. 17, 2011

(65) Prior Publication Data
US 2012/0213757 A1    Aug. 23, 2012

(30) Foreign Application Priority Data
Aug. 17, 2010  (EP) ..................................... 10380106

(51) Int. Cl.
*A61K 38/43*   (2006.01)
*A23L 1/30*    (2006.01)
*A23L 1/302*   (2006.01)
*A23L 1/305*   (2006.01)
*A61K 31/70*   (2006.01)

(52) U.S. Cl.
CPC . *A23L 1/30* (2013.01); *A23L 1/302* (2013.01); *A23L 1/3012* (2013.01); *A23L 1/3051* (2013.01); *A61K 31/70* (2013.01)

(58) Field of Classification Search
None
See application file for complete search history.

(56) References Cited

U.S. PATENT DOCUMENTS

| | | | | |
|---|---|---|---|---|
| 5,567,424 | A  * | 10/1996 | Hastings | 424/195.17 |
| 7,429,569 | B2 * | 9/2008  | Halevie-Goldman | 514/43 |
| 2003/0021772 | A1 * | 1/2003 | Birkmayer | 424/94.1 |
| 2004/0259809 | A1 * | 12/2004 | Gonzales | 514/23 |

OTHER PUBLICATIONS

Molyneux et al., The bioavailability of coenzyme Q10 supplements available in New Zealand differs markedly, Journal of the New Zealand Medical Association 117 (1203), Oct. 8, 2004.*
Addington, l-serine: treatment for chronic fatigue syndrome, http://www.prohealth.com/library/showarticle.cfm?libid=428, Feb. 2, 1999, accessed Jul. 19, 2012.*

* cited by examiner

*Primary Examiner* — Patricia A Leith
*Assistant Examiner* — Erin M Bowers
(74) *Attorney, Agent, or Firm* — RatnerPrestia

(57) ABSTRACT

New dietary supplement composition comprising, as active ingredients:
NADH and/or $NAD^+$
Coenzyme Q10
Vitamin C (Ascorbic Acid)
Serine and/or Phosphoserine
to be used for stimulating/improving/increasing the production of naturally occurring adrenaline, thus reducing sleepiness caused by particular drugs intake. The dietary supplement according to the present invention is particularly advantageous for professional drivers and persons who usually take drugs having sleepiness as major side effect.

8 Claims, No Drawings

NUTRITIONAL SUPPLEMENT COMPOSITION

The present application claims benefit of EP 10380106.4 filed Aug. 17, 2010.

Several nutritional compositions are known from the recent years, particularly advantageous compositions formulated, for example, to reduce physical and mental fatigue, to enhance activity, to improve recovery from activity, to promote muscle performance, to increase energy substrates, to contribute to improved antioxidant defenses (i.e., reduce oxidative stress or lipid peroxidation, conserve anti-oxidants in the sera), to enhance mood, to assist in preventing primary and secondary diseases associated with fatigue and muscle atrophy associated with inactivity, to improve nervous system (i.e., neuronal) and musculoskeletal (i.e., increase skeletal muscle protein synthesis, increase satellite cells) health, and to contribute to improvements in overall health. The compositions according to the above, are usually in the form of dietary supplement and are to be taken in addition to usual alimentary programs.

For example, several compositions containing NADH are available on the market as dietary supplement.

Nicotinamide adenine dinucleotide, abbreviated $NAD^+$, is a coenzyme found in all living cells. The compound is a dinucleotide, since it consists of two nucleotides joined through their phosphate groups, with one nucleotide containing an adenine base and the other containing nicotinamide.

In metabolism, $NAD^+$ is involved in redox reactions, carrying electrons from one reaction to another. The coenzyme is, therefore, found in two forms in cells: $NAD^+$, that is an oxidizing agent—it accepts electrons from other molecules and becomes reduced forming NADH, which can then be used as a reducing agent to donate electrons. These electron transfer reactions are the main function of $NAD^+$. However, it is also used in other cellular processes, notably as a substrate of enzymes that add or remove chemical groups from proteins. Because of the importance of these functions, the enzymes involved in $NAD^+$ metabolism are targets for drug discovery.

In organisms, $NAD^+$ can be synthesized from simple building-blocks (de novo) from the amino acids tryptophan or aspartic acid. In an alternative fashion, more complex components of the coenzymes are taken up from food as the vitamin called niacin.

NADH is directly involved in the body's cellular immune defensive system.

ADH, biologically known as Coenzyme 1 (as it is the most important co-enzyme, also known as Co-E1), is thus necessary for thousands of biochemical reactions within the body and is found naturally in every living cell.

As a dietary supplement NADH is currently commercialized to help boost energy and add vitality to the human body. Nutritional compositions containing NADH may also aid in combating the effects of disorders such as fibromyalgia, that is a physical disorder that causes the sensory system to become hyperaware of environmental stimuli such as pain, and to alleviate the symptoms of certain energetic disorders such as fatigue, particularly chronic fatigue syndrome, which is often related to stress and which is defined as a condition in which a patient has persistent fatigue not attributable to any other cause.

Other dietary supplement are known, comprising for example Coenzyme Q10, that is also known as ubiquinone, ubidecarenone, coenzyme Q, and abbreviated at times to $CoQ_{10}$ CoQ, Q10, or Q. This compound is a 1,4-benzoquinone, where Q refers to the quinone chemical group, and 10 refers to the number of isoprenyl chemical subunits.

This oil-soluble substance is present in most eukaryotic cells, primarily in the mitochondria. It is a component of the electron transport chain and participates in aerobic cellular respiration, generating energy in the form of ATP.

Because of its ability to transfer electrons and, therefore, act as an antioxidant, $CoQ_{10}$ is used as a dietary supplement, for example in the following applications: mitochondrial disorders, heart failure, headaches, cardiac arrest, blood pressure, periodontal disease, Parkinson's disease.

Compositions containing both NADH and CoQ10 are also known as dietary supplement, as they are indicated because of their capacity to supply energy, miming energy production mechanisms and antioxidant activity that usually occur in the human body.

Another product that is widely used as a dietary supplement is Vitamin C, also called ascorbic acid, that is a water-soluble nutrient that is easily excreted from the body when not needed. Its so critical to living creatures that almost all mammals can use their own cells to make it.

Humans vary greatly in their vitamin C requirement. Its natural for one person to need 10 times as much vitamin C as another person; and a person's age and health status can dramatically change his or her need for vitamin C.

Most forms of cardiovascular disease, joint disease, cancer, eye disease, thyroid disease, liver disease, and lung disease require special emphasis on vitamin C intake. The process of aging itself requires special attention to vitamin C. In addition to these broader categories, several specific health conditions also require special emphasis on vitamin C. These specific health conditions include, for example, asthenia, acne, Alzheimer's disease, asthma, depression, diabetes, Parkinson's disease. The beneficial effects of ascorbic acid are due to its intervention in the tyrosine metabolism, leading, at the end of the biochemical pathway, to the formation of adrenalin.

Dietary supplements typically contain vitamin C in the form of ascorbic acid. Because vitamin C is better absorbed in the presence of flavonoids, many supplement manufacturers also add flavonoids to their formulas.

Buffered versions of vitamin C are also commonly available. These buffered forms usually combine vitamin C with minerals like calcium, magnesium, or potassium. Buffered vitamin C may be helpful for individuals who have stomach sensitivity, or who are taking higher doses of the supplement.

Also widely available is a metabolite complex form of vitamin C, in which ascorbic acid is combined with several of its naturally occurring metabolites including dehydroascorbate, threonate, aldonic acids and also CoQ10.

Compositions containing NADH and Vitamin C are also known as dietary supplement, indicated as adjuvant in the fatigue situations and as excellent antioxidants.

It is an object of the present invention to provide new compositions comprising different compatible active ingredients, able to contribute to restore and/or increase the energy levels of the human beings.

Another object of the present invention is to provide new compositions comprising different compatible active ingredients, to be used as dietary supplements for human beings, particularly in those situations where it is necessary a high level of attention.

Still another object of the invention is to provide new compositions comprising different compatible active ingredients, able to restore/stimulate major biochemical pathways that are pointed to the production of energy and/or to the increase of attention in the human body, without occurring in adverse side effects.

Still another object of the present invention is to provide new compositions comprising different compatible active ingredients, able to stimulate/improve/increase the production of naturally occurring adrenaline, thus solving the problem due to the impossibility of oral administering adrenaline.

Another object of the present invention is to provide new compositions comprising different compatible active ingredients, to be used as dietary supplement and nutritional products also in addition to usual drugs and medicaments, without having unexpected side effects.

These and also other objects are achieved by a new dietary supplement composition comprising, as active ingredients:

NADH and/or $NAD^+$
Coenzyme Q10
Vitamin C (Ascorbic Acid)
Serine and/or Phosphoserine.

The composition according to the present invention further comprises usual eccipients and components necessary for its formulation as a dietary supplement.

A dietary supplement, also known as food supplement or nutritional supplement, is a preparation intended to supplement the diet and provide nutrients, such as vitamins, minerals, fiber, fatty acids, or amino acids, that may be missing or may not be consumed in sufficient quantity in a person's diet. Some countries define dietary supplements as foods, while in others they are defined as drugs or natural health products.

According to the present invention, each of the above listed active ingredient of the composition is essential for the aim claimed.

Serine (abbreviated as Ser or S) is an organic compound with the formula $HO_2CCH(NH_2)CH_2OH$. It is one of the naturally occurring proteinogenic amino acids and is important in metabolism in that it participates in the biosynthesis of purines and pyrimidines. It is the precursor to several amino acids including glycine and cysteine, and tryptophan in bacteria. It is also the precursor to numerous of other metabolites, including sphingolipids and folate, which is the principal donor of one-carbon fragments in biosynthesis.

While serine turns into glycine, it originates a kind of "active formaldehyde". This reaction is one of the most important reactions producing C1 fragments (for example methyl, formaldehyde and formate groups).

Serine is also a biological precursor of colamine and plays an important role in the metabolism of carbon hydrates, mainly through two different pathways. Serine plays an important role in the catalytic function of many enzymes. It has been shown to occur in the active sites of chymotrypsin, trypsin, and many other enzymes. A As a constituent (residue) of proteins, its side chain can undergo O-linked glycosylation, which may be functionally related to diabetes. It is one of three amino acid residues that are commonly phosphorylated by kinases during cell signaling in eukaryotes. Phosphorylated serine residues are often referred to as phosphoserine. Serine proteases are a common type of protease.

Serine is a water soluble compound, while, for example, it is not soluble in ethanol.

The composition according to the present invention shows a surprising effect as a dietary (nutritional) supplement due to a synergic effect of its essential active ingredients and, particularly, due to the addition of serine and/or phosphoserine to the other components, i.e. NADH and/or $NAD^+$, Coenzyme Q10 and Vitamin C (Ascorbic Acid).

It has observed, in fact, that the composition according to the present invention can positively influence main naturally occurring oxidation-reduction processes, transferring electrons to enzymes that act as biocatalysts in these reactions. For example, one of these reactions is dopamine hydroxylation to give noradrenaline and its prosecution process to give adrenaline as final product.

Adrenaline sympathicomimetic effect are significant for example during emotional crisis or where it is necessary to alert or prepare the body to an emergency situation. In fact, adrenaline acts as a stimulant of the sympathetic system and is able to produce positive effects on the central nervous system.

It has to be noted that it is not possible to administer adrenaline by oral administration, because it undergoes oxidation and degradation/conjugation during the gastrointestinal passage and by the liver.

Therefore, it has been found, according to the present invention, that a supplementary dietary composition comprising serine and/or phosphoserine, NADH and/or $NAD^+$, Coenzyme Q10 and Vitamin C (Ascorbic Acid) as active and essential ingredients, can surprisingly and significantly promote the natural production of adrenaline in the human body, while avoiding undesired side effects.

According to the present invention therefore, the composition comprising serine and/or phosphoserine, NADH and/or $NAD^+$, Coenzyme Q10 and Vitamin C (Ascorbic Acid) as active and essential ingredients, is advantageously used as a dietary supplement in cases where there is the need of improving and/or recovering energy, for example during a convalescence. In this case, for example, it has been observed that the composition according to the invention acts as an stimulator in cases of weakness, fatigue, sleepiness and the like.

For example, always according to the invention, the composition can be advantageously used as adjuvant dietary supplement for those persons that need particular attention, such as professional drivers (cars, trucks and the like).

Another related use of the composition according to the invention is directed, for example, to the reduction of sleepiness caused by particular drugs intake, thus resolving a very widespread problem. For example, those forced to take antistaminic drugs suffer very relevant problems of sleepiness. On the market, associations between antistaminic and stimulating drugs already exist; however, the exciting action of the stimulating drug, necessary to contrast the antistaminic drug side effect, is difficult to be modulated and very often cause even worse side effect, keeping the patient awake too much time and thus causing an associate fatigue syndrome.

The association of an antistaminic drug intake with a dietary supplement according to the present invention, would allow to physiologically modulate the stimulating effect, thus avoiding an over response and the presence of additional side effects.

According to the present invention, the wording "association" or "combination" means that the composition according to the invention and the antistaminic (or other already existing drug which have sleepiness as major side effect) are administered together in separate forms as different formulations, or in different moments also in separate forms and different formulations or in a single form or formulation, while both existing in separate e different entities within the formulation.

The availability of a product able to induce a natural and endogenous stimulator effect, which can effectively contrast the sleepiness side effect of certain drugs, is a long felt need, particularly for those who must drive cars, trucks, trains and planes for professional reasons.

In Spain for example, about 5% of traffic accidents are related with drugs intake. At least about 17% of drivers declare to be on drug treatment and it is estimated that at least 26.4% of this cases involve drugs whose predicted side effects are related to sleepiness. This problem is weight down by the fact that 76.5% of the patients declare not to have been advised on possible side effects of the drugs they are taking in relation to their capability to drive. Another related problem is due to the fact that most of the patients taking drugs with side effects related to sleepiness, do not refer to a doctor before and during the drug intake, and thus are not warned about possible adverse side effects.

The composition according to the present invention represents a great improvement in the dietary supplements designed for acting in restoring/inducing body energy in the human body. In fact, the surprising effect of reducing sleepiness while still inducing a better energy feeling, result in a innovative nutritional supplement with respect to the existing products, which are active on the energy levels, but do not have any effect with respect to sleepiness. It has to be noted, as already said above, that the composition according to the invention, is able to induce a positive response of the human body with respect to sleepiness, without causing adverse side effect of fatigue or the like, as the response of the body is a kind of "natural", "endogenous" response and it is not caused by additional drugs.

The suggested use of this dietary supplement is therefore in all cases where an increase/restore of the body energy is required, together with a recover of the attention levels affected by several causes, among which, for example, the intake of drugs with adverse side effects related to sleepiness.

Always according to the invention, some examples of compositions containing serine and/or phosphoserine, NADH and/or NAD$^+$, Coenzyme Q10 and Vitamin C (Ascorbic Acid) as active ingredients, are here below indicated in Table 1.

TABLE 1

| Active ingredient | Formula 1 | Formula 2 | Formula 3 | Formula 4 |
|---|---|---|---|---|
| NAD+ or NADH | 10 mg | 5-10 mg | 10 mg | 5-20 mg |
| CoQ10 | 100 mg | 60-100 mg | 90 mg | 200 mg |
| Serine or fosfatidilserine | 40 mg | 40 mg | 50 mg | 80 mg |
| Vitamine C (Ascorbic acid) | 90 mg | 140 mg | 100 mg | 150 mg |
| Excipients q.s.p | Aprox 250-500 mg | Aprox 300 mg | Aprox 350 mg | Aprox 500 mg |

It is intended that the above formulations are given only as examples of dietary supplement compositions according to the invention and they do not in any way represent a limitation of the scope of protection.

The dietary supplement compositions according to the invention can be formulated in all forms suitable for oral administration, for example tablets, film-coated tablets, sublingual tablets, dispersible tablet, buccal dispersible tablets, sachets, capsules, powder, pellets, micro-pellets, soluble effervescent granules.

Always according to the invention, the dietary supplement compositions can also be formulated in all forms suitable for rectal, nasal administration, or any other suitable administration.

The invention claimed is:

1. A dietary supplement composition consisting of:
   10 mg of NADH;
   100 mg of coenzyme Q10;
   200 mg of vitamin C; and
   50 mg of serine.

2. A method of supplementing the diet of a human comprising administering the dietary supplement of claim 1 to said human.

3. A method of restoring the energy level of a human or increasing the energy level of a human comprising administering the dietary supplement of claim 1 to a person in need of said restoring or increasing such that the energy level of said human is restored or increased.

4. A method of restoring or stimulating human production or human attention comprising administering the dietary supplement of claim 1 to a person in need of said restoring or stimulating such that the production or attention of said human is restored or stimulated.

5. A method of stimulating or improving or increasing the production of naturally occurring adrenaline in a human comprising administering the dietary supplement of claim 1 to a person in need of said stimulating or improving or increasing such that the production of naturally occurring adrenaline of said human is stimulated or improved or increased.

6. A method of reducing sleepiness associated with ingestion of a drug in a person comprising administering the dietary supplement of claim 1 to a person in need of reducing such that the sleepiness is reduced.

7. The method of claim 6 wherein the dietary supplement is administered with said drug.

8. The method of claim 7 wherein said drug is an antihistaminic drug.

\* \* \* \* \*